US 8,856,331 B2

(12) United States Patent
Coyer et al.

(10) Patent No.: US 8,856,331 B2
(45) Date of Patent: Oct. 7, 2014

(54) APPARATUS AND METHODS OF DISTRIBUTING CONTENT AND RECEIVING SELECTED CONTENT BASED ON USER PERSONALIZATION INFORMATION

(75) Inventors: James D. Coyer, Encinitas, CA (US); Charles C. Childress, Austin, TX (US); Michael T. Coad, San Diego, CA (US); Charles R. Wiltgen, Encinitas, CA (US)

(73) Assignee: QUALCOMM Incorporated, San Diego, CA (US)

( * ) Notice: Subject to any disclaimer, the term of this patent is extended or adjusted under 35 U.S.C. 154(b) by 1131 days.

(21) Appl. No.: 11/561,310

(22) Filed: Nov. 17, 2006

(65) Prior Publication Data

US 2007/0204004 A1 Aug. 30, 2007

Related U.S. Application Data

(60) Provisional application No. 60/739,471, filed on Nov. 23, 2005, provisional application No. 60/789,444, filed on Apr. 4, 2006.

(51) Int. Cl.
| | | |
|---|---|---|
| *G06F 15/173* | (2006.01) | |
| *H04L 29/06* | (2006.01) | |
| *H04L 12/911* | (2013.01) | |
| *G06Q 10/04* | (2012.01) | |
| *H04L 29/08* | (2006.01) | |
| *H04L 12/26* | (2006.01) | |
| *G06F 11/34* | (2006.01) | |
| *G06F 19/24* | (2011.01) | |

(52) U.S. Cl.
CPC ........... *H04L 29/06027* (2013.01); *H04L 47/70* (2013.01); *G06Q 10/04* (2013.01); *H04L 67/22* (2013.01); *H04L 43/00* (2013.01); *G06F 11/3438* (2013.01); *G06F 11/3452* (2013.01); *G06F 19/24* (2013.01); *H04L 65/4076* (2013.01); *H04L 65/607* (2013.01); *H04L 67/306* (2013.01)
USPC .................. 709/226; 725/35; 725/34; 725/32

(58) Field of Classification Search
CPC .............. G06F 15/173; G06F 11/3438; G06F 11/3452; G06F 19/24; H04L 29/06; H04L 67/22; H04L 43/00; H04L 47/70; H04M 2215/0108; H04N 21/25; H04H 60/46; H04W 8/18; G06Q 10/04
USPC ............................... 709/226; 707/732, 784, 9
See application file for complete search history.

(56) References Cited

U.S. PATENT DOCUMENTS

| 6,055,364 | A | 4/2000 | Speakman et al. | |
|---|---|---|---|---|
| 6,330,610 | B1 * | 12/2001 | Docter et al. | ................. 709/229 |

(Continued)

FOREIGN PATENT DOCUMENTS

| CN | 1627311 A | 6/2005 |
|---|---|---|
| EP | 1679896 A1 | 7/2006 |

(Continued)

OTHER PUBLICATIONS

International Search Report, PCT/US06/061214—International Search Authority—European Patent Office, Feb. 1, 2008.

(Continued)

*Primary Examiner* — O. C. Vostal
(74) *Attorney, Agent, or Firm* — The Marbury Law Group, PLLC

(57) ABSTRACT

Apparatus and methods include the distribution of a plurality of content, at least one of which is tagged with descriptive metadata. Further, the apparatus and methods include selecting content from the plurality of content based on a match between a personalized content preference descriptor stored on the device and the tagged content. Thus, the selected content represents content likely to be applicable or relevant, and/or of interest, to the user associated with the personalized content preference descriptor.

13 Claims, 8 Drawing Sheets

(56) References Cited

U.S. PATENT DOCUMENTS

| | | | |
|---|---|---|---|
| 6,484,148 B1* | 11/2002 | Boyd | 705/14.64 |
| 6,505,169 B1* | 1/2003 | Bhagavath et al. | 705/14.66 |
| 6,757,365 B1* | 6/2004 | Bogard | 379/88.17 |
| 6,986,154 B1* | 1/2006 | Price et al. | 725/46 |
| 7,013,365 B2* | 3/2006 | Arnouse | 711/115 |
| 7,035,653 B2* | 4/2006 | Simon et al. | 455/466 |
| 7,136,932 B1* | 11/2006 | Schneider | 709/245 |
| 7,139,834 B1* | 11/2006 | Albanese et al. | 709/238 |
| 7,173,933 B1* | 2/2007 | O'Rourke et al. | 370/389 |
| 7,395,054 B2* | 7/2008 | Kitamura et al. | 455/418 |
| 7,469,250 B2* | 12/2008 | Bazot et al. | 1/1 |
| 7,966,395 B1* | 6/2011 | Pope et al. | 709/224 |
| 2002/0107941 A1* | 8/2002 | Katz et al. | 709/219 |
| 2002/0111172 A1* | 8/2002 | DeWolf et al. | 455/456 |
| 2002/0119775 A1* | 8/2002 | Mukherjee et al. | 455/435 |
| 2002/0124050 A1* | 9/2002 | Middeljans | 709/203 |
| 2002/0161890 A1* | 10/2002 | Chen | 709/226 |
| 2002/0194603 A1 | 12/2002 | Connelly | |
| 2003/0028451 A1* | 2/2003 | Ananian | 705/27 |
| 2003/0061611 A1* | 3/2003 | Pendakur | 725/46 |
| 2003/0088613 A1* | 5/2003 | Goldschmidt Iki et al. | 709/202 |
| 2003/0120534 A1* | 6/2003 | Giacchetti et al. | 705/10 |
| 2003/0120817 A1* | 6/2003 | Ott et al. | 709/249 |
| 2003/0135605 A1 | 7/2003 | Pendakur | |
| 2003/0191816 A1* | 10/2003 | Landress et al. | 709/219 |
| 2003/0219708 A1 | 11/2003 | Janevski et al. | |
| 2004/0024886 A1* | 2/2004 | Saxena | 709/229 |
| 2004/0181604 A1* | 9/2004 | Immonen | 709/232 |
| 2004/0221018 A1* | 11/2004 | Ji | 709/217 |
| 2005/0002407 A1* | 1/2005 | Shaheen et al. | 370/401 |
| 2005/0022229 A1* | 1/2005 | Gabriel et al. | 725/28 |
| 2005/0038876 A1* | 2/2005 | Chaudhuri | 709/219 |
| 2005/0044229 A1* | 2/2005 | Brown et al. | 709/226 |
| 2005/0076012 A1* | 4/2005 | Manber et al. | 707/3 |
| 2005/0083899 A1* | 4/2005 | Babbar et al. | 370/342 |
| 2005/0095999 A1* | 5/2005 | Haberman et al. | 455/179.1 |
| 2005/0096036 A1* | 5/2005 | Haberman et al. | 455/422.1 |
| 2005/0096039 A1* | 5/2005 | Haberman et al. | 455/422.1 |
| 2005/0096043 A1* | 5/2005 | Haberman et al. | 455/422.1 |
| 2005/0096047 A1* | 5/2005 | Haberman et al. | 455/432.3 |
| 2005/0097595 A1* | 5/2005 | Lipsanen et al. | 725/25 |
| 2005/0113075 A1* | 5/2005 | Haberman et al. | 455/414.2 |
| 2005/0204381 A1* | 9/2005 | Ludvig et al. | 725/34 |
| 2005/0246231 A1* | 11/2005 | Shkedi | 705/14 |
| 2006/0085419 A1* | 4/2006 | Rosen | 707/9 |
| 2006/0090185 A1* | 4/2006 | Zito et al. | 725/46 |
| 2006/0095331 A1* | 5/2006 | O'Malley et al. | 705/22 |
| 2006/0126556 A1* | 6/2006 | Jiang et al. | 370/328 |
| 2006/0143674 A1* | 6/2006 | Jones et al. | 725/113 |
| 2006/0165092 A1* | 7/2006 | Wilson et al. | 370/395.21 |
| 2006/0167944 A1* | 7/2006 | Baker | 707/104.1 |
| 2006/0247943 A1* | 11/2006 | Kapoor | 705/1 |
| 2006/0256731 A1* | 11/2006 | Jennings et al. | 370/252 |
| 2006/0270419 A1* | 11/2006 | Crowley et al. | 455/456.2 |
| 2007/0033531 A1* | 2/2007 | Marsh | 715/738 |
| 2007/0053358 A1* | 3/2007 | Aaltonen | 370/392 |
| 2007/0061199 A1* | 3/2007 | Montgomery et al. | 705/14 |
| 2007/0066341 A1* | 3/2007 | Silverbrook et al. | 455/550.1 |
| 2007/0067297 A1* | 3/2007 | Kublickis | 707/9 |
| 2007/0079325 A1* | 4/2007 | de Heer | 725/32 |
| 2008/0016533 A1* | 1/2008 | Rothschild | 725/60 |
| 2008/0027692 A1* | 1/2008 | Fables et al. | 703/6 |
| 2008/0126420 A1* | 5/2008 | Wright et al. | 707/104.1 |
| 2008/0133716 A1* | 6/2008 | Rao et al. | 709/220 |
| 2008/0215884 A1* | 9/2008 | Yonemoto | 713/168 |
| 2009/0070201 A1* | 3/2009 | Hodges et al. | 705/11 |
| 2009/0190505 A1* | 7/2009 | Gassewitz et al. | 370/259 |
| 2010/0017455 A1* | 1/2010 | Svendsen et al. | 709/202 |
| 2010/0281364 A1* | 11/2010 | Sidman | 715/713 |
| 2010/0332583 A1* | 12/2010 | Szabo | 709/202 |
| 2011/0034121 A1* | 2/2011 | Ng et al. | 455/3.06 |
| 2012/0155358 A1* | 6/2012 | Hao et al. | 370/312 |
| 2012/0198420 A1* | 8/2012 | Pein | 717/124 |
| 2012/0259722 A1* | 10/2012 | Mikurak | 705/26.1 |
| 2013/0007152 A1* | 1/2013 | Alspector et al. | 709/206 |
| 2013/0073738 A1* | 3/2013 | Reisman | 709/227 |

FOREIGN PATENT DOCUMENTS

| | | |
|---|---|---|
| JP | H11164217 A | 6/1999 |
| JP | 2003173341 (A) | 6/2003 |
| JP | 2005509229 A | 4/2005 |
| JP | 2005509964 A | 4/2005 |
| JP | 2005176312 A | 6/2005 |
| JP | 2005521299 (T) | 7/2005 |
| JP | 2005293195 A | 10/2005 |
| JP | 2005312024 (A) | 11/2005 |
| TW | I244075 | 11/2005 |
| WO | 9937045 | 7/1999 |
| WO | WO 99/35778 A2 | 7/1999 |
| WO | 03034255 | 4/2003 |
| WO | 03043333 A1 | 5/2003 |

OTHER PUBLICATIONS

International Preliminary Report on Patentability, PCT/US06/061214—The International Bureau of WIPO, May 27, 2008.
Written Opinion, PCT/US06/061214—International Searching Authority,.European Patent Office—Feb. 1, 2008.
Search Report—ROC (Taiwan) Patent Application No. 095143426, Feb. 13, 2010, Taiwan, ROC.
Translation of Office Action in Japanese Application No. 2008-542526, Dec. 21, 2010, Suzuye & Suzuye, Japan.
European Search Report; European Application No. 12005596; Search Authority—Munich; Sep. 10, 2012.

* cited by examiner

APPARATUS AND METHODS OF DISTRIBUTING CONTENT AND RECEIVING SELECTED CONTENT BASED ON USER PERSONALIZATION INFORMATION

CLAIM OF PRIORITY UNDER 35 U.S. C. §119

The present Application for Patent claims priority to Provisional Application No. 60/789,444 entitled "Apparatus And Methods Of Distributing Content And Receiving Selected Content Based On User Personalization Information" filed Apr. 4, 2006, and Provisional Application No. 60/739,471 entitled "Catchcasting For Multicast Networks" filed Nov. 23, 2005, both assigned to the assignee hereof and both hereby expressly incorporated by reference herein.

BACKGROUND

The described aspects relate to media distribution systems, and more particularly, to the delivery of one or more categorized content and the receipt of selected ones of the categorized content based on user preferences.

Communication networks have been designed to deliver content to recipients. For example, one type of communication network comprises a unicast system, which delivers content to one recipient at a time, i.e. on a one-to-one basis. Because of this one-to-one nature, a user of a unicast system nay request to receive content of interest to that user only. When desiring to communicate a single piece of content to a large number of recipients, however, unicast systems are relatively inefficient. For example, in a unicast system, the delivery of identical content to many endpoints is resource intensive, since each endpoint must redundantly request the same content and reserve a predetermined amount of bandwidth, thereby consuming valuable network resources and limiting scalability. In contrast, multicast systems are communication networks which transmit information to multiple recipients at the same time. Multicast delivery technologies address the problem of cost effective delivery of content usable by a large number of network endpoints. Despite its network utilization advantages, however, multicast technology presents a challenge in addressing personalized and narrow-interest content delivery.

Further, the desire for mobile consumption of content is increasing along with the increasing popularity and functionality of mobile communication devices.

Additionally, to catch the attention of the user and provide a more efficient use of the user's time it is desirable for content to be directed to the specific interests or preferences of the device user. Current methods of targeting content to users are inefficient, as these methods typically select content based on characterizations of an entire group of users receiving a multicast transmission.

Thus, improved systems and method of distributing and receiving content of interest to the device user are desired.

SUMMARY

The described aspects include apparatus and methods for distributing a plurality of content at least one of which is categorized, defined and/or described via metadata. Further, the apparatus and methods include selecting content from the plurality of content based on a correspondence between a user characteristic, such as a personalized content preference descriptor and the categorized content. For example, user characteristics may include characteristics such as device location, time, user demographics, user psychographics, affinity, user-preferred content categories, and any other data which may provide a relationship between the device user and content likely to be applicable, relevant and/or of interest to the device. Thus, the selected content represents content likely to be applicable, relevant and/or of interest to the user having one or more user characteristics, such as may be defined by one or more personalized content preference descriptors.

A method of receiving content comprising obtaining, on a wireless device, a personalized content preference descriptor based on user characteristic information on the wireless device. The method further comprising obtaining, on the wireless device, a predetermined content descriptor corresponding to one of a plurality of content. Also, the method comprising obtaining, on the wireless device, a multicast transmission of the plurality of content associated with a content supplier. Further, the method comprising selecting, at the wireless device, one from the plurality of content based on a match between at least a portion of the respective predetermined content descriptor and the personalized content preference descriptor. Additionally, the method further comprises processing, on the wireless device, the selected content.

In a related aspect, a machine-readable medium comprises instructions stored thereon comprising sets of instructions corresponding to the actions of the above-stated method. In a further related aspect, at least one processor is configured to perform the actions of the above-stated method.

In another aspect, a wireless device comprises means for obtaining a personalized content preference descriptor based on user characteristic information on the wireless device. Further, the wireless device comprises means for obtaining a predetermined content descriptor corresponding to one of a plurality of content. Also, the wireless device comprises means for obtaining a multicast transmission of the plurality of content associated with a content supplier. Further, the wireless device comprises means for selecting one from the plurality of content based on a match between at least a portion of the respective predetermined content descriptor and the personalized content preference descriptor. Additionally, the wireless device comprises means for processing the selected content.

In yet another aspect, a wireless device comprises a memory, a communications module and a processor. Further, the memory comprises a personalized content preference descriptor, a predetermined content descriptor and a content selection engine. The personalized content preference descriptor is based on user characteristic information on the wireless device. The predetermined content descriptor corresponds to one of a plurality of content. The content selection engine is operable to select at least one from the plurality of content based on a match between at least a portion of the respective predetermined content descriptor and the personalized content preference descriptor. Additionally, the communications module is operable to obtain a multicast transmission of the plurality of content associated with a content supplier. Further, the processor is in communication with the memory and the communications module, and the processor is operable to execute the content selection engine to select one from the plurality of content. Additionally, the processor is operable to further process the selected content.

In a further aspect, a method of distributing content comprises obtaining, on a distribution system, a plurality of predetermined content descriptors defined by a content supplier. The method further comprises obtaining, at the distribution system, a plurality of content. Also, the method comprises obtaining, at the distribution system, an association between at least one of the plurality of predetermined content descriptors and one of the plurality of content. Additionally, the method comprises multicasting, from the distribution system, the plurality of content and the association to a plurality of devices. In this aspect, the association is operative to cause the selective processing of the one of the plurality of content on one of the devices based on a match between the associated predetermined content descriptor and a personalized content preference descriptor stored at the respective device.

In a related aspect, a machine-readable medium comprises instructions stored thereon comprising sets of instructions corresponding to the actions of the above-stated method. In another related aspect, at least one processor is configured to perform the actions of the above-stated method.

In an additional aspect, an apparatus for distributing content comprises a memory, a multicast mechanism and a processor. The memory comprises a plurality of content, a plurality of predetermined content descriptors, and an association between at least one of the plurality of content and at least one of the plurality of predetermined content descriptors. In this aspect, the plurality of predetermined content descriptors are defined by a content supplier. The multicast mechanism is operable to transmit the plurality of content and the association to a plurality of devices. The processor is operable to execute the multicast mechanism to initiate the transmission of the plurality of content and the association. In this aspect, the association is operative to cause the selective processing of the at least one of the plurality of content on one of the devices based on a match between the associated predetermined content descriptor and a personalized content preference descriptor stored at the respective device.

DETAILED DESCRIPTION

The present apparatus and methods now will be described more fully with reference to the accompanying drawings. The apparatus and methods may be embodied in many different forms, however, and should not be construed as limited to the aspects set forth herein. Additionally, throughout this description, like numbers refer to like elements.

Figure 1:
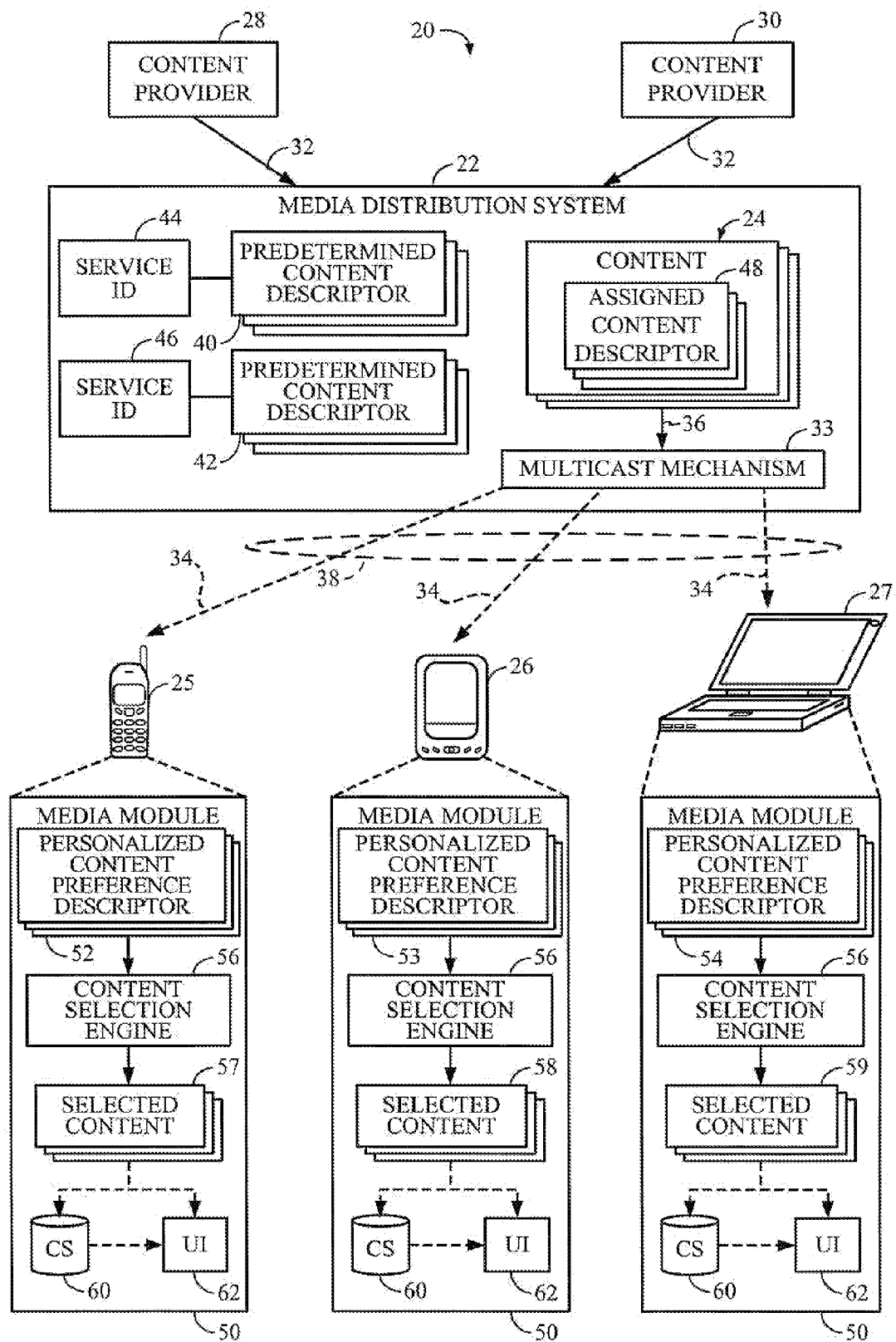
FIG. 1 is a schematic diagram of one aspect of a communication network operable for the distribution and selective receipt of media content based on one or more user characteristics.

Referring to FIG. 1, in some aspects, a communication network 20 comprises a media distribution system 22 operable to distribute a plurality of content 24 to a plurality of wireless devices 25-27, wherein at least some of the devices are operable to selectively execute and/or store selected content based on device user-specific personalization information. In particular, the user-specific personalization information includes personalized content preference information. As such, the present apparatus and methods enable a device to download multicast content, including an advertisement, which is more likely to be of interest to the device user when compared to content supplied according to other targeting methods.

It should be noted that although three devices 25-27 are illustrated in FIG. 1, virtually any number and/or type of devices are suitable for use in the aspects described herein.

Further, network 20 comprises one or more content providers 28, 30 operable to provide all or some portion of the plurality of content 24 for distribution to users in network 20. For example, the plurality of content 24 supplied by content providers 28, 30 may comprise at least one of video, audio, multimedia content, real-time content, non real-time content also referred to as "clips," scripts, programs, data or any other type of suitable content. The plurality of content 24 may include one or any combination of subscribed to programming, ad hoc and/or on-demand programming, advertising or any other form of content presented during a break within and/or simultaneously with other content. In some aspects, content providers 28, 30 communicate with media distribution system 22 via a communication link 32, which may comprise any suitable type of wired and/or wireless communication interface.

In some aspects, media distribution system 22 may comprise a transport system that operates to create and transport a multimedia content flow 34, including one or more media services 36, across one or more data network 38. For example, such a transport system may include a multicast mechanism 33. In some aspects of multicasting, each flow 34 is a logical stream within a "multiplex," which is a set of flows available in a given geographical area. Further, media service 36 comprises one or some combination of the plurality of content 24, where a media service customized for a specific retailer may be referred to as a "channel." As such, each flow 34 is able to deliver the same service 36 to a plurality of endpoints at the same time, as the flow is available to any device tuning in to the proper frequency, thereby avoiding scalability issues. Therefore, media distribution system 22 may be operable to transport media content in a one-to-one fashion.

Additionally, in the described aspects, media distribution system 20 may distribute one or more predetermined content descriptors 40, 42 to the plurality of wireless devices 25-27. The one or more predetermined content descriptors 40, 42 may be stored separately from or embedded within the respective content. Further, the one or more predetermined content descriptors 40, 42 may comprise, but are not limited to, one or some combination of a category, a name, a code, an identifier and/or any metadata relating to and/or that can be used to describe a respective one of the plurality of content 24. In some aspects, for example, the one or more predetermined content descriptors 40, 42 may be customized and grouped into a set for each service 36, and thus are associated with a respective unique service identification (ID) 44, 46. For example, in some aspects, one or more "content suppliers" associated with each service 36 may define each respective set of predetermined content descriptor 40, 42. As used herein, the term "content supplier" may include one or any combination of a content provider, a content retailer, a billing and customer service provider, a network service provider, a media distributor such as media distribution system 22, and any party in or related to the chain of distribution of content to the device user. It should be noted, however, that in some aspects, such as when dealing with a new type or theme of content, the device user may define a content descriptor which may be used by the content supplier.

Correspondingly, at least one of the plurality of content 24 is associated with one or more assigned content descriptors 48, which may be individually defined for the given content, and/or which may be selected from one or more predetermined content descriptors 40, 42 associated with a respective one or more service IDs 44, 46. For instance, one or more of the content suppliers associated with a respective one of the plurality of content 24 may define or select one or more content descriptors 40, 42 as the respective assigned content descriptor(s) 48 or a respective piece of content. Further, in some aspects, one or more assigned content descriptors 48 may be associated with a respective one or more service IDs 44, 46, and hence with a respective service or channel.

Further, respective ones of the plurality of wireless devices 25-27, such as ones having a predetermined media module 50, may be operable to obtain one or more user personalized content preferences descriptors 52-54 that provide a basis for choosing content likely to be of interest to a device user from among a plurality of content receivable by the respective device. In some aspects, user personalized content preference descriptors 52-54 may be selected from among the received one or more predetermined content descriptors 40, 42 for one or more respective services 36. In other aspects, user personalized content preference descriptors 52-54 may be logically determined and/or predicted and related to the received one or more predetermined content descriptors 40, 42. For example, user personalized content preference descriptors 52-54 may be based on one or any combination of user-indicated preferences, user-derived preferences based on user/device behavior, location, local device time, user content consumption behavior, a wireless network carrier associated with the device, user demographic information, psychographic information or personality traits of the device user or one or more device users associated with the device user such as identified friends, family and/or co-workers, affinity information, user device characteristics, etc. In any case, each of the one or more respective user personalized content preference descriptors 52-54 may vary from device to device and from user to user depending on user preferences.

Wireless devices 25-27 may further include a content selection engine 56 operable to identify, such as within a given flow 34, respective ones of the plurality of content 24 having one or more assigned content descriptors 48 that correspond to and/or match with the respective one or more user personalized content preference descriptors 52-54. Further one or more of the user personalized content preference descriptors 52-54 may be globally applied to any incoming content, and/or selectively applied to a given service 36 associated with a respective service identifier (ID) 44, 46. In any case, as a result, content selection engine 56 is operable to extract the identified matching content, referred to respectively as selected content 57-59, from the respective flow 34 of one or a plurality of content 24. As such, respective selected content 57-59 may vary from device to device and from user to user depending on user preferences as reflected in the respective one or more personalized content preference descriptors 52-54.

Additionally, content selection engine 56 may be operable to initiate further processing of selected content 57-59 on the respective wireless device 25-27. For example, content selection engine 56 may initiate the retention of selected content 57-59 on the respective device 25-27, such as in a data repository, memory and/or content storage mechanism 60. Alternately, or in addition, content selection engine 56 may initiate the presentation of selected content 57-59 on the respective device 25-27, such as via a user interface 62, including, for example, a display, a speaker, a haptic feedback mechanism, and combinations thereof.

Therefore, in various aspects, the apparatus and methods of the described communication network 20 provide for the distribution of a plurality of content, with at least some content having or associated with one or more descriptors, i.e. metadata describing the content. Further, in some aspects, the apparatus and methods may provide for the separate distribution of a plurality of predetermined content descriptors which may be potentially associated with the content. Further, in various aspects, the apparatus and methods of the described communication network 20 provide for the retention and presentation of content selected by the wireless device from a multicast flow of the plurality of content based on a correspondence and/or match between personalized content preference descriptors and one or more content descriptors associated with the respective content. Thus, a user of a wireless device is provided with content, filtered and extracted by the wireless device from a group of content, likely to be of interest to the user based on predetermined user preferences.

Figure 2:
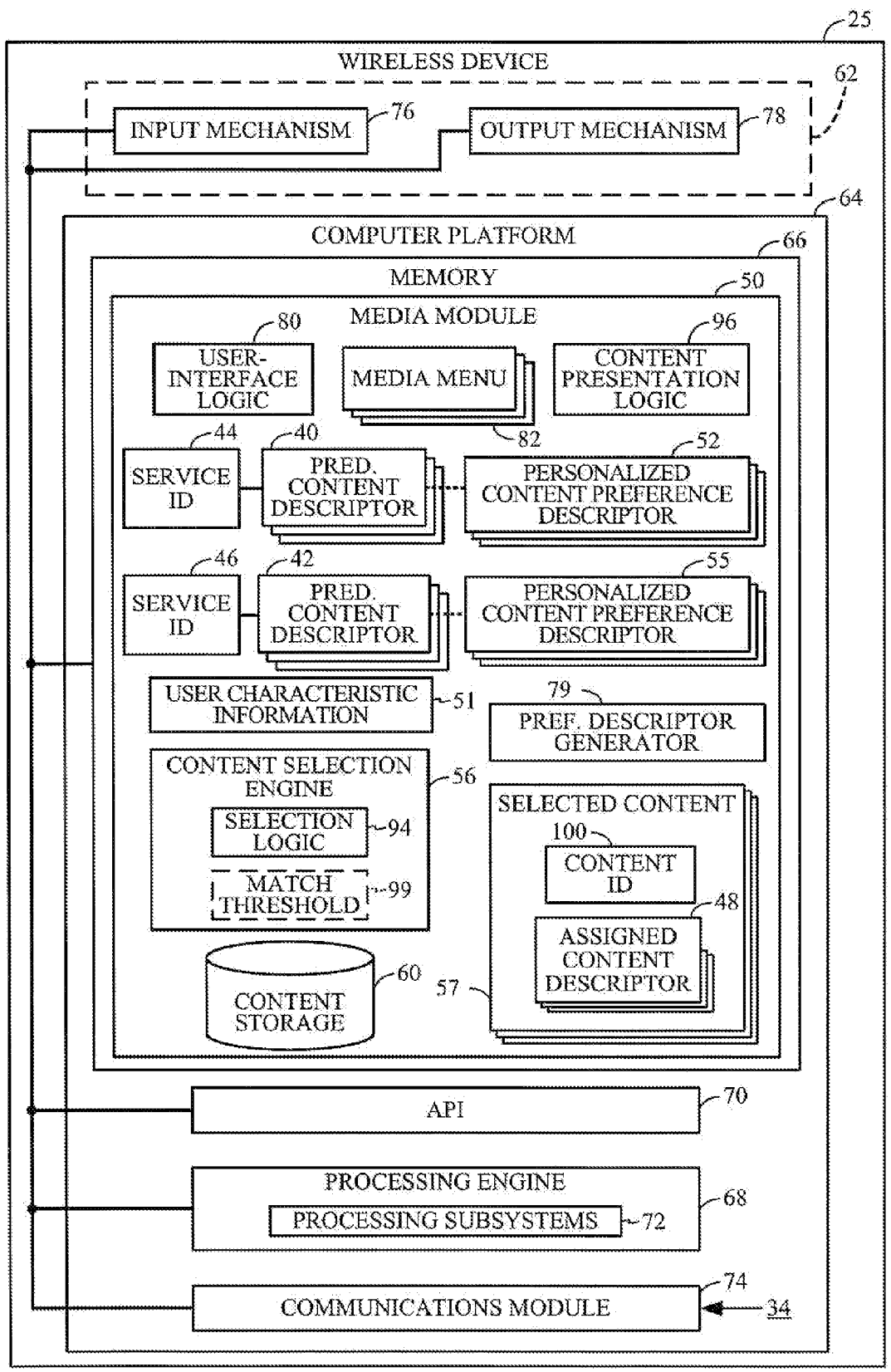
FIG. 2 is a schematic diagram of one aspect of an architecture of the wireless device from FIG. 1.

Referring to FIG. 2, in some aspects, representative components of any of wireless devices 25-27, such as wireless device 25, are illustrated. It should be noted that although wireless devices 25-27 are respectively illustrated as cellular telephone 25, Personal Digital Assistant (PDA) 26 and laptop computer 27, a wireless device may include any type of computerized, wireless device, such as a two-way pager, a portable gaming device, a portable music device, any other type of portable computer, and even a separate computer platform having a wireless communications portal, and which also may have a wired connection to a network or the Internet. The wireless device can be a remote-slave, a remote sensor, a diagnostic tool, a data relay, and any other device that does not have an end-user thereof but simply communicates data across a wireless network. The present apparatus and methods can accordingly be performed on any form of wireless device or computer module, including a wired or wireless communication portal, including without limitation, wireless modems, PCMCIA cards, access terminals, personal computers, telephones, or any combination or sub-combination thereof.

Wireless device 25 may include a computer platform 64 that can transmit data across a network, such as data network 38, and that can receive and execute routines and applications and optionally display data transmitted from any network device or other computer device connected to the network or connected to wireless device 25. For example, computer platform, 64 may be embodied in hardware, firmware, software, data, executable instructions, and combinations thereof. Computer platform 64 may include a memory 66, which may comprise volatile and nonvolatile memory such as read-only and/or random-access memory (RAM and ROM), EPROM, EEPROM, flash cards, or any memory common to computer platforms. Further, memory 66 may include one or more flash memory cells, or may be any secondary or tertiary storage device, such as magnetic media, optical media, tape, or soft or hard disk, including removable memory mechanisms.

Further, computer platform 64 also, may include a processing engine 68, which may be one or more of an application-specific integrated circuit ("ASIC"), a chipset, a processor, a logic circuit, and any other data processing device. In some aspects, processing engine 68, or other processor such as an ASIC, may execute an application programming interface, (API) layer 70 that interfaces with any resident programs, such as media module 50, stored in memory 66 of wireless device 25. API 70 is typically a runtime environment executing on the respective wireless device. One such runtime environment is Binary Runtime Environment for Wireless® (BREW®) software developed by Qualcomm, Inc., of San Diego, Calif. Other runtime environments may be utilized that, for example, operate to control the execution of applications on wireless computing devices.

Additionally, processing engine 68 may include various processing subsystems 72 embodied in hardware, firmware, software, data, executable instructions and combinations thereof, which enable the functionality of wireless device 25 and the operability of the wireless device on network 38. For example, processing subsystems 72 allow for initiating and maintaining communications, and exchanging data, with media distribution system 22 and/or other networked devices. In aspects in which the wireless device is defined as a cellular telephone 25, for example, the communications processing engine 68 may additionally include one or a combination of processing subsytems 72, such as: sound, non-volatile memory, file system, transmit, receive, searcher, layer 1, layer 2, layer 3, main control, remote procedure, handset, power management, digital signal processor, messaging, call manage, Bluetooth® system, Bluetooth® LPOS, position engine, user interface, sleep, data services, security, authentication, USIM/SIM, voice services, vocoder, messaging, graphics, USB, multimedia, etc. For the disclosed aspects, processing subsystems 72 of processing engine 68 may include any subsystem components that interact with applications executing on computer platform 64 that enable the functionality described herein. For example, processing subsystems 72 may include any subsystem components that receive data reads and data writes from API 70 on behalf of the media module 50.

Further, computer platform 64 may include a communications module 74 embodied in hardware, firmware, software, data, executable instructions and combinations thereof, which enables communications among the various components of wireless device 25, as well as between wireless device 25 and network 38. For example, in a cellular telephone aspect, communication module 74 may include the requisite hardware, firmware, software, data, executable instructions and combinations thereof, including transmit and receive chain components for establishing a wireless communication connection. Additionally, for example, communications module 74 may include any input/output port associated with the respective device.

Further, in some aspects, for example, communication module 74 may be operable to receive the one or more predetermined content descriptors 40 and/or 42 and either forward them to media module 50 or provide media module 50 with access to them. Similarly, for example, communication module 74 is operable to receive the plurality of content 24 and the associated respective one or more assigned content descriptors 48, if any, from media distribution system 22 and forward them, or provide access to them, to content selection engine 56. Subsequently, for example, communications module 74 is operable to forward selected content 57-59, respectively, to other device components for further processing based on instructions from content selection engine 56.

Additionally, wireless device 25 may include one or more input mechanisms 76 for generating inputs into wireless device, and one or more output mechanisms 78 for generating information for consumption by the user of the wireless device. For example, input mechanism 76 may include a mechanism such as a key or keyboard, a navigation mechanism, a mouse, a touch-screen display, a microphone in association with a voice recognition module, etc. In certain aspects, input mechanism 76 may provide for user input to activate or interact with an application or module on the wireless device. Further, for example, output mechanism 78 may include a display, an audio speaker, a haptic feedback mechanism, etc. Further, user interface 602 may comprise one or any combination of input mechanism 76 and/or output mechanism 78.

Additionally, computer platform 64 may further include media module 50, as described above. For example, media module 50 may embodied in one or more of hardware, firmware, software, data, executable instructions and combinations thereof. Media module 50 is operable to manage, perform and/or initiate all or at least some portion of the user personalization-related or personalized content preference-related, input/output-related, media content management-related and media content presentation-related activities discussed herein. For example, media module 50 may comprise a client application and/or a client agent associated with media distribution system 22.

In some aspects, for example, media module 50 may include user interface logic 80 operable to generate one or more of a plurality of media menus 82 suitable for interfacing with a device-user to carry-out various content management functions, such as personalization selection activities, channel/service subscription activities, execution and storage of content, etc.

Figure 3:
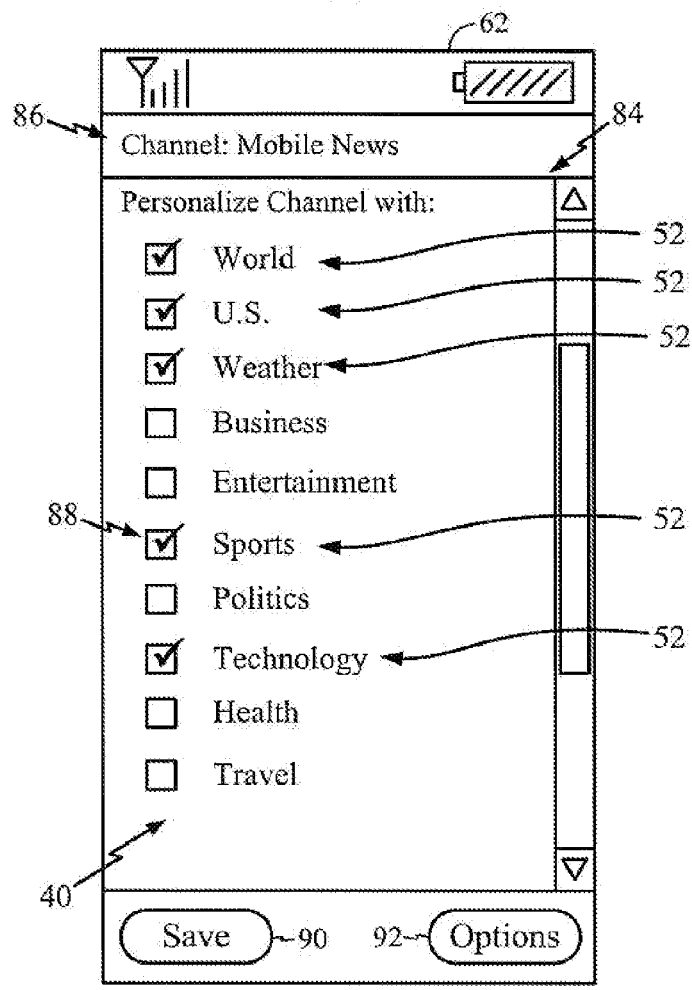
FIG. 3 is a view of one aspect of a user preference selection menu presentable on the wireless device of FIG. 1.

For example, referring to FIG. 3, in some aspects where user personalization information is collected from the device user in order to generate one or more personalized content preference descriptors 52-54, user interface logic 80 may generate a user personalization menu 84. Menu 84 may be presented to the device user, such as on a display-type user interface 62, and may be operable to provide the device user with the one or more predetermined content descriptors 40 (or 42), for example, which may be associated with a respective channel 86. As mentioned above, channel 86 comprises a given service 36 customized for a content supplier, and as such a channel may be further associated with a corresponding service ID 44 (or 46) (FIG. 1). For example, upon first activating a given channel 86, user interface logic 80 may automatically, or based on a user request, obtain user preference selection menu 84 from the plurality of media menus 82 (FIG. 2) and present it to the device user. As such, a user may utilize one or more input mechanisms 76 (FIG. 2) to provide a selection indicator 88, such as a highlight, a checkmark, etc., to indicate the selection of one or more predetermined content descriptors 40. As such, in some aspects, a selected one of the predetermined content descriptors 40 may be thereby defined as or associated with a user personalized content preference descriptor 52. Further, for example, user preference selection menu 84 may include selectable functions, such as a "Save" virtual button 90 to save the indicated selections and/or an "Options" virtual button 92 to access an alternate one of the plurality of media menus 82 (FIG. 2), such as a help menu and/or a menu to identify a number of pieces of content to save and/or an amount of memory to dedicate for selected content from the respective channel. Thus, in some aspects, device-user identification of one or more predetermined content descriptors 40 from user personalization menu 84 results in the generation of one or more user personalized content preference descriptors 52.

Alternatively, in other aspects, the device user may individually define one or more user personalized content preference descriptors 52-54 by typing in a name, a description, etc. These non-service provider-defined content descriptors may be combined with any selected predetermined content descriptors and saved as the global and/or service- or channel-based user personalized content preference descriptors 52. Further, in some aspects, user interface logic 80 may include algorithms, decision-making routines, fuzzy logic, heuristic relationships, neural networks, etc., which may be operable to associate non-service provider-defined content descriptors with one or more predetermined content descriptors and store this relationship as the user personalized content preference descriptors 52.

Figure 4:
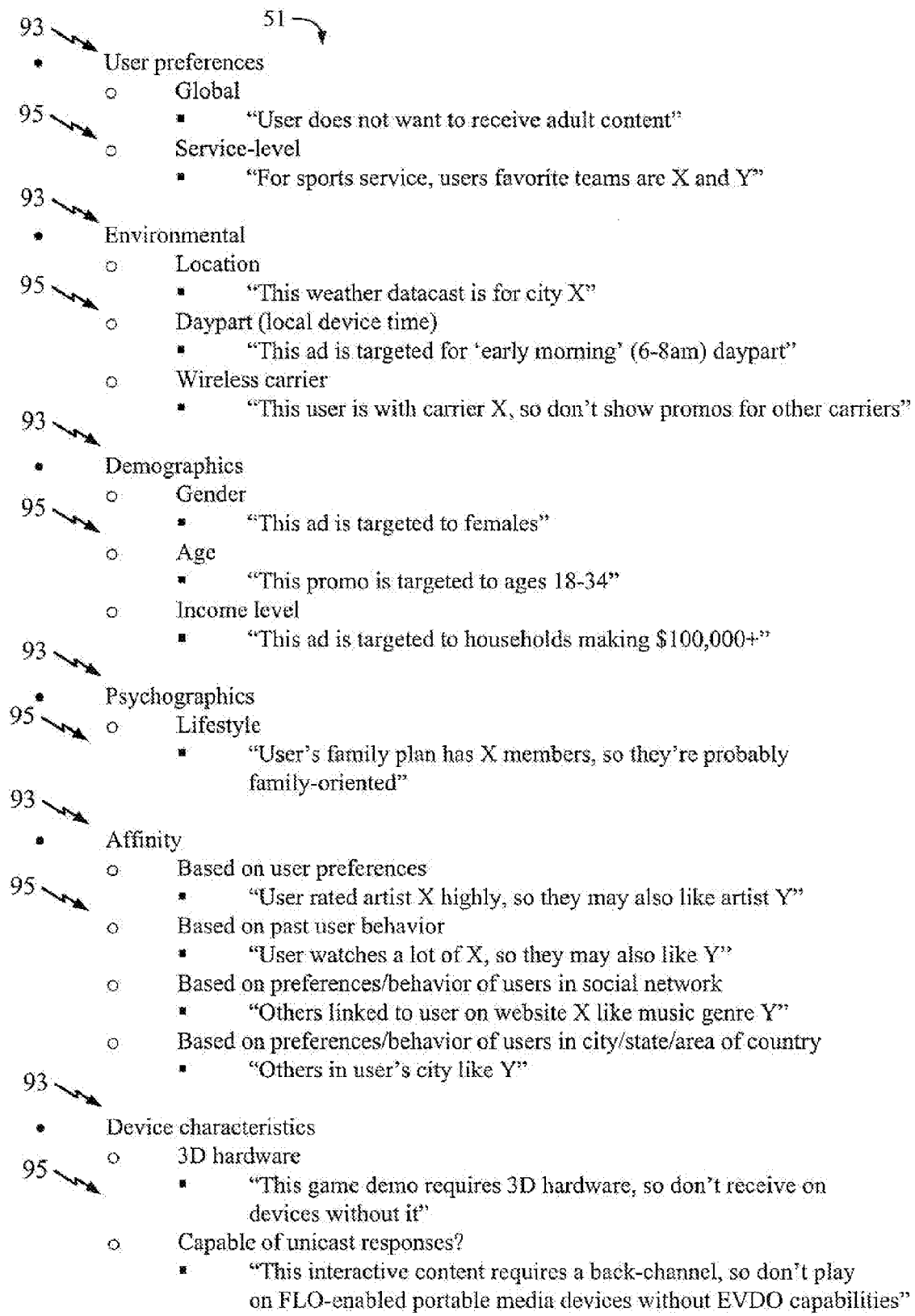
FIG. 4 is a view of a list of user character-based information and/or content descriptors, relating to apparatus and methods of FIG. 1.

In still other alternatives, referring to FIGS. 2 and 4, media module 50 may include a preference descriptor generator 79 (FIG. 2) and/or user interface logic 80 (FIG. 2), which may include at least one of algorithms, decision-making routines, fuzzy logic, heuristic relationships, neural networks, etc. which may be operable to associate user characteristic information 51 (FIGS. 2 and 4) with one or more predetermined content descriptors 40 (and/or 42; FIG. 2). Further, preference descriptor generator 79 and/or user interface logic 80 are operable to store one or more of these relationships as one or more user personalized content preference descriptors 52 (and/or 55). As mentioned above, user characteristic information 51 may include any information relating to the respective device user and/or the respective device. For example, user characteristic information 51 may include, but is not limited to, one or any combination of: user preferences such as a content category, content type, content genre, etc, such as global-level and/or at a channel-/service-level; environmental information such as device location, local device time and date, and affiliated wireless carrier; demographics such as age, gender, income level; psychogaphics or trait information of the device user or any number of other users related to the device user; affinity-based information such as a prediction as to what content the device user may like based on predetermined factors such as past usage behavior, behavior of friends/family/co-workers, etc.; device hardware and/or software characteristics; and device-based user behavioral information, such as what applications, data and content are used/consumed, when and for how long, etc. It should be noted that user characteristic information 51 may include any other information which may provide an insight into content preferred by, and applicable, relevant, and/or of interest to the device user. In some aspects, user characteristic information 51 may be resident in memory 66 of the respective wireless device 25, while in other aspects all or some portion of user characteristic information 51 is available from other devices, such as from a content supplier-related device.

Further, as noted above, in some aspects, for one device/user, a respective personalized content preference descriptor 52 may be associated with a given service ID 44 (and hence a given channel or service), and is selected from a corresponding channel/service-specific set of one or more predetermined content descriptors 40. Similarly, for another device/user, another respective personalized content preference descriptor 53 may be associated with another, different given service ID 46 (and hence another, different given channel or service), and may be selected from a corresponding channel/service-specific set of one or more content categories 42. For example, for a mobile news channel or service (see FIG. 3), the predetermined content descriptors 40 may include, but are not limited to, categories such as World news, U.S. news, Weather news, Business news, Sports news, Politics news, Technology news, Health news and Travel news. In another example, such as for a baseball-related channel or service, the predetermined content descriptors may include, but are not limited to, categories such as one category for every team, a category for highlights from a respective division or league, a category for all highlights, etc. In yet another example, for a music channel or service, the predetermined content descriptors may include, but are not limited to, categories such as a category for a respective genre, such as Rock, Country, Hip-Hop, Rhythm and Blues, etc., a category corresponding to an artist name, a category corresponding to an album name, etc.

Additionally, as discussed above, media module 50 may include content selection engine 56 operable to extract one or more selected content 57 from the plurality of media content 24 (FIG. 1) within flow 34 received by communications module 74. In particular, content selection engine 56 may include selection logic 94, such as predetermined algorithms, rules, fuzzy logic, decision-making routines, etc., operable to determine a match and/or some level of correspondence between a respective assigned content descriptor 48 (FIG. 1) associated, with one of the plurality of content 24 and the corresponding one or more personalized content preference descriptors 52-54 associated with a respective device user. A "match" as used herein includes, but is not limited to, one or a combination of an exact match, at least a matching portion, a likelihood of a match, and a percentage of a match, where a predetermined match threshold 99 may be utilized to determine a match. For example, the match threshold may indicate a predetermined one or more personalized content descriptors, or a predetermined number or percentage of personalized content descriptors, which must correlate to content descriptors of the respective contents in order for the content to be selected as a match. Further, in some aspects, based on an identified match, selection logic 94 may initiate the storage and/or presentation of selected content 57, such as based on the content type, e.g. real-time or non-real-time, which may be identified by the one or more assigned content descriptors 48.

Referring to FIG. 4, for example, in one non-limiting aspect, media module 50 (FIG. 2) may access a database of user characteristic information 51. Such a database of information 51 may include categories 93 and subcategories 95 which may be utilized as and/or associated with content descriptors 40, 42 and/or as personalized content descriptors 52-54. Content selection engine 56 (FIGS. 1 and 2) may consider all or any portion of user characteristic information 51 in determining whether or not to chose the respective content as selected content 57.

Additionally, media module 50 may include content presentation logic 96 operable to generate one or more of the plurality of media menus 82 suitable for interfacing with a device-user to manage media module 50, selected content 57 and generate the presentation and/or manage the storage of the content on wireless device 25.

Figure 5:
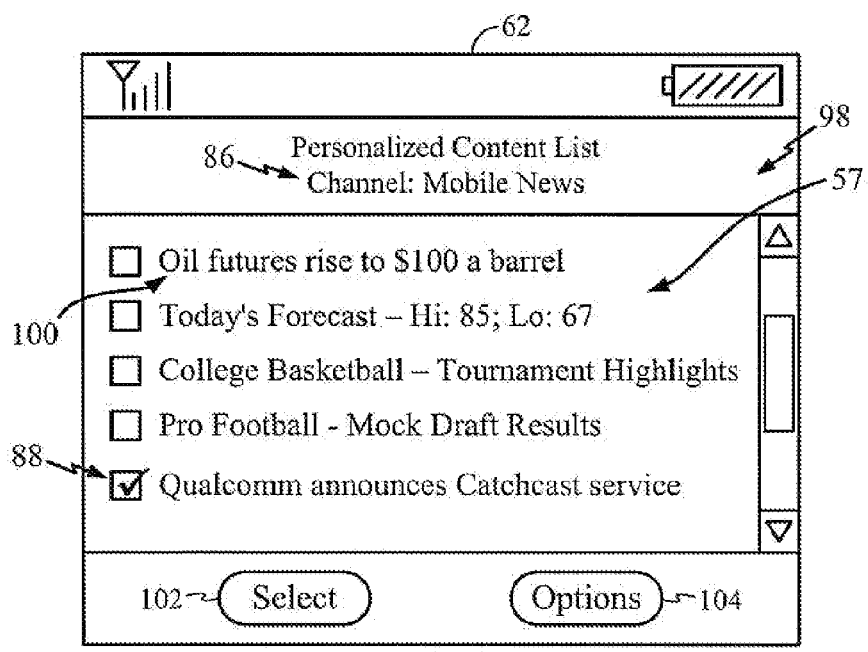
FIG. 5 is a view of one aspect of a personalized content list menu presentable on the wireless device of FIG. 1.

For example, referring to FIG. 5, content presentation logic 96 may generate a personalized content list menu 98, such as on a display-type user interface 62, that presents the device-user with the one or more selected content 57 (or 58 or 59). For example, in some aspects, personalized content list menu 98 lists selected content 57 associated with a respective channel 86, while in other aspects the list may include selected content from more than one channel or from all channels. Personalized content list menu 98 comprises a personalized list of content based on the wireless device-based matching activity as described above with regard to content selection engine 56. For instance, upon initialization of media module 50, content presentation logic 96 may automatically or in response to a device-user input received by input mechanism 76 (FIG. 2) obtain personalized content list menu 98 from the plurality of media menus 82 (FIG. 2) and present it to the device-user. In some aspects, for example, content presentation logic 96 is operable to locate selected content 57 and parse predetermined information, such as a content identifier (ID) 100 and/or assigned content descriptor 48, and present this information to the device-user. For example, content ID 100 may include, but is not limited to, one or some combination of a name, a title, a unique identifier, etc. associated with the corresponding content. In some aspects, it may be desirable for assigned content descriptor 48 (FIG. 1) to comprise content ID 100, or vice versa, while in other aspects it may be desirable for assigned content descriptor 48 and content ID 100 to be mutually exclusive. In any case, a user may utilize one or more input mechanisms 76 (FIG. 2) to provide a selection indicator 88, such as a highlight, a checkmark, etc., to indicate the selection of one or more of the listed content. Further, for example, content presentation logic 96 may include selectable functions, such as a "Select" virtual button 102 to initialize the choice, execution and presentation of the indicated selection(s), such as via output mechanism 78 (FIG. 2). Additionally, the selectable functions may further include an "Options" virtual button 104 to access other menus, such as a help menu, a content management menu for deleting content and/or adjusting content-related settings, such as a number of content and/or an amount of memory to utilize to save content, a predetermined amount of time to store content, etc.

Referring back to FIG. 2, content storage 60 associated with media module 50 may provide long-term and/or short-term storage for any selected content 57. For example, long-term storage may be desired for selected content 57 that the device-user desires to retain or desires to execute in the future, while short-term storage may include memory space associated with executing content as well as any other short-term storage. Content storage 60 may comprise volatile and non-volatile memory such as read-only and/or random-access memory (RAM and ROM), EPROM, EEPROM, flash cards, or any memory common to computer platforms. Further, content storage 60 may include one or more flash memory cells, or may be any secondary or tertiary storage device, such as magnetic media, optical media, tape, or soft or hard disk, including removable memory mechanisms.

Figure 6:
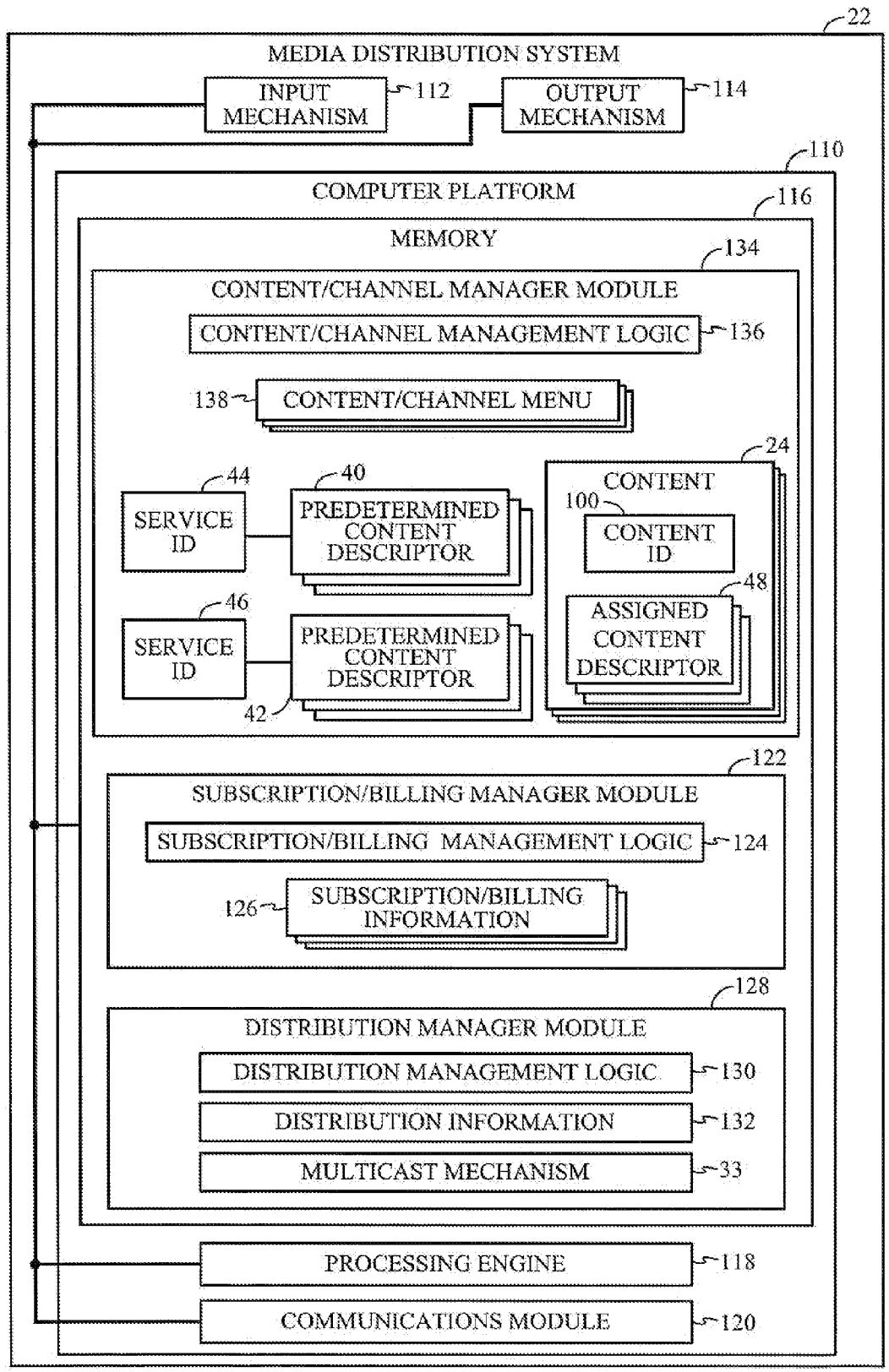
FIG. 6 is a schematic diagram of one aspect of an architecture of the media distribution system of FIG. 1.

Referring to FIG. 6, in some aspects, media distribution system (MDS) 22 may comprise one or any combination of any type of hardware, software, firmware, server, personal computer, mini computer, mainframe computer, and generally any special purpose and/or general purpose computing device. Further, there can be separate servers or computer devices and/or networks associated with MDS 22 that work in concert to receive, manipulate and provide data in usable formats to parties, and/or to provide a separate layer of control in the data flow between devices and networks and MDS 22.

MDS 22 may comprise a computer platform 110 comprising one or a plurality of resident and/or distributed computer platforms that can receive and transmit data, receive and execute software applications and generate and/or display data and/or content. For example, computer platform 110 may be embodied in hardware, firmware, software, data, executable instructions and combinations thereof.

Computer platform 110 may be associated with an input mechanism 112 for generating inputs into MDS 22, and output mechanism 114 for generating information for consumption by a local and/or remote operator of MDS 22. For example, input mechanism 112 may include a mechanism such as a key or keyboard, a mouse, a touch-screen display, voice recognition module, etc. Further, for example, output mechanism 114 may be a display, an audio speaker, a haptic feedback mechanism, etc. Additionally, input mechanism 112 may be a remote device, such as a remote computer, dumb terminal and/or workstation, which has access to MDS 22. In some aspects, for example, input mechanism 112 and/or output mechanism 114 may be utilized by one or more operators to manage one or more of the receipt and categorization of content received from content providers; the establishment, maintenance and deletion of channels, tiers and packages associated with one or more content retailers and/or billing and customer service providers; the establishment, maintenance and deletion of subscription and billing information; and the distribution of content through media flows.

Further, computer platform 110 may include one or more data repositories and/or memories 116, which may comprise volatile and nonvolatile memory such as read-only and/or random-access memory (RAM and ROM), EPROM, EEPROM, flash cards, or any memory common to computer platforms. Further, memory 116 may include one or more flash memory cells, or may be any secondary or tertiary storage device, such as magnetic media, optical media, tape, or soft or hard disk, including removable memory mechanisms. In several aspects, for example, memory 116 includes the one or more content servers.

Further, computer platform 110 also includes a processing engine 118, which may be an application-specific integrated circuit ("ASIC"), or other chipset, processor, logic circuit or other data processing device for carrying out executable instructions.

Computer platform 110 may further include a communications module 120 embodied in one or more of hardware, firmware, software, data executable instructions and combinations thereof, that enables wired and wireless communications among the various components of MDS 22, and between MDS 22 and network 38 and wireless devices 25-27. For example communications module 120 may include a transceiver module for wireless communications with wireless devices 25-27 and/or network 38.

Further, computer platform 110 may include one or more subscription/billing manager modules 122 which operate to manage all of the media content subscription and billing functions associated with MDS 22. For example, subscription/billing manager module 122 may be embodied in one or more of hardware, processors, software, firmware, data and/or other set of executable instructions. Further, in some aspects, subscription/billing manager module 122 includes subscription/billing management logic 124 that provides MDS 22 with the capability to receive, store and manipulate subscription and billing information 126. For example, subscription/billing information 126 may include subscriber/device-user identity, address and payment-related information, corresponding wireless device identifier information, subscriber account information, package, tier, and channel information, etc. Further, subscription/billing management logic 124 may be operable to receive, process and transmit subscription related information, such as subscription requests, the corresponding approvals or denials, and the management of digital rights based on an approved subscription request for a channel, tier or package of content.

Additionally, computer platform 110 may include one or more distribution manager modules 128 which operate to manage all of the media content distribution functions associated with MDS 22. For example, distribution manager module 128 may be embodied in one or more of hardware, processors, software, firmware, data and/or other set of executable instructions. Further, in some aspects, distribution manager module 128 includes distribution management logic 130 that provides MDS 22 with the capability to receive, store and manipulate distribution information 132 and control the distribution of content. For example, distribution information 134 may include information and/or relative associations between information such as one or a combination of flows, flow regions, networks, content, channels, services, tiers, packages, content suppliers, etc. Further, distribution management logic 130 may be operable to receive and process content and content-related information, as well as content retailer-specific information, such as customization information, auxiliary services, auxiliary presentations, channel information, tier information and package information. Additionally, distribution management logic 130 may be operable to initiate the transmission of flows 34, such as via multicast mechanism 33. For example, multicast mechanism 33 may comprise all or some portion of a multicast system such as a Forward Link Only (FLO) network, including the MEDIA-FLO™ System available from Qualcomm, Inc. of San Diego, Calif.

Additionally, computer platform 110 may include one or more content/channel manager modules 134 which operate to manage operations relating to the media content received and the channel/services distributed by MDS 22. For example, content/channel manager module 134 may be embodied in one or more of hardware, processors, software, firmware, data and/or other set of executable instructions. Further, in some aspects, content/channel manager module 134 includes content/channel management logic 136 that provides MDS 22 with the capability to receive, store and manipulate the plurality of content 24 and the respective services 34 (FIG. 1) and/or channels 86 (FIG. 3), as well as the associated content-related information, such as assigned content descriptors 48, content IDs 100, and the associated channel/service information, such as the associated content, tier and package information.

In some aspects, for example, content/channel management logic 136 is operable to generate one or more of a plurality of content and channel/service menus 138 suitable for interfacing with a user of MDS 22 to carry-out various content and channel/service management functions, such as channel/service definitions, category definition activities and content descriptor activities, etc.

Figure 7:
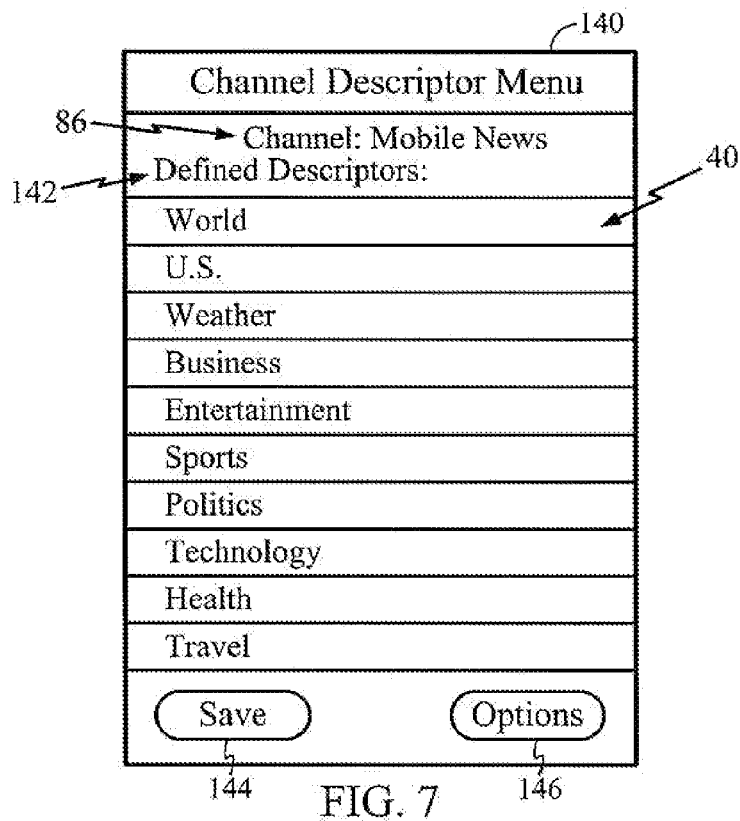
FIG. 7 is a view of one aspect of a channel/service categorization menu available, in some aspects, through interaction with the media distribution system of FIG. 1.

For example, referring to FIG. 7, content/channel management logic 136 may generate a channel/service descriptor menu 140, such as on a display-type user interface associated with input mechanism 112 (FIG. 6) and/or output mechanism 114 (FIG. 6), which allows the user to define predetermined content descriptors 40 (or 42) associated with a respective channel 86 (or service 36, FIG. 1). For example, upon activating a given channel 86 (or service 36), content/channel management logic 136 may automatically retrieve channel/service descriptor menu 140 from the plurality of content and channel/service menus 138 (FIG. 6) and present it to the user. Alternately, menu 140 may be retrieved based on received user inputs. In any case, a user may utilize one or more input mechanisms 112 (FIG. 6) to create a list of defined descriptors 142. For example, a user may individually define a descriptor by typing in a name, a description, a descriptor code which may be referenced to a database of descriptors, and/or selecting from a list of content descriptors obtained from a content descriptor database. Further, for example, channel/service descriptor menu 140 may include selectable functions, such as "Save" virtual button 144 to save the listed categories and/or an "Options" virtual button 146 to access an alternate one of the plurality of content and channel/service menus 138 (FIG. 6), such as a help menu and/or a menu to enter or define a new descriptor, edit or delete an existing descriptor, etc. As such, the list of defined descriptors 142 can be created and/or modified, and saved to comprise predetermined content descriptors 40, which can be associated with the respective channel 86. Thus, in some aspects, user interaction with channel/service descriptor menu 140 results in the generation of one or more predetermined content descriptors 40 corresponding to a respective channel 86 and/or service 36 (FIG. 1).

Figure 8:
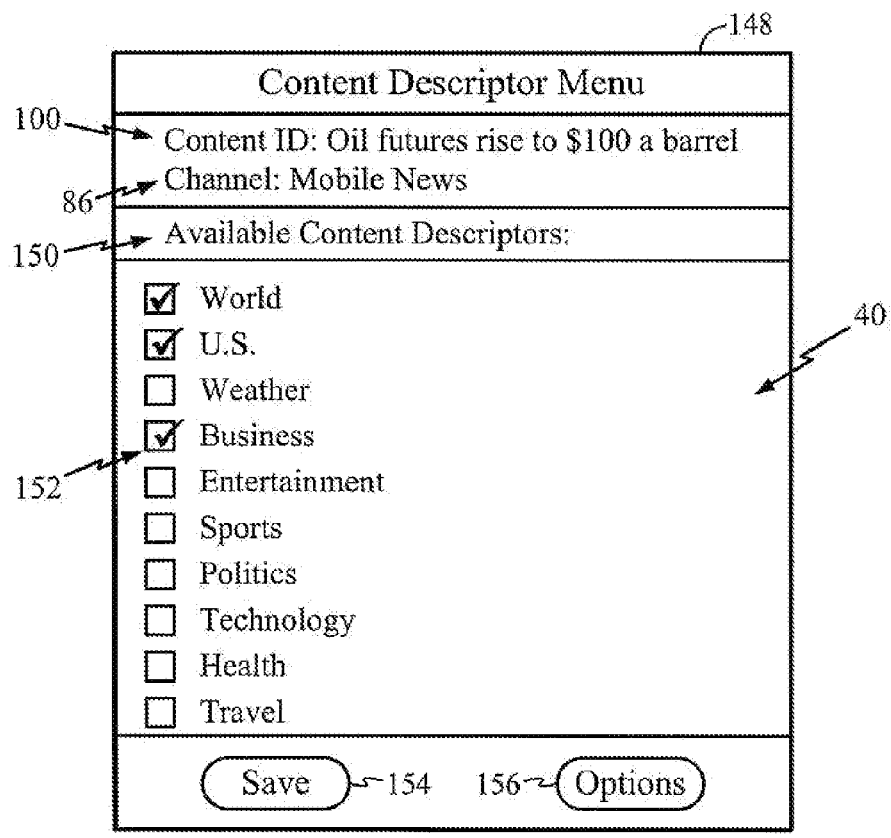
FIG. 8 is a view of one aspect of a content categorization menu available, in some aspects, through interaction with the media distribution system of FIG. 1.

Additionally, referring to FIG. 8, in some aspects, content/channel management logic 136 is operable to allow a user to categorize and/or describe a given one of the plurality of content 24. Content/channel management logic 136 may generate a content descriptor menu 148 which enables the user to select from a list of available content descriptors 150, and/or personally define one or more content descriptors, to associate with a given content ID 100 as the one or more respective assigned content descriptor 48. For example, content descriptor menu 148 may be presented to a user of MDS 22 on a display-type user interface associated with input mechanism 112 (FIG. 6) and/or output mechanism 114 (FIG. 6). Additionally, in some aspects, content/channel management logic 136 is operable, based on an identified channel 86 and/or service 36 (FIG. 1), to populate the list of available content descriptors 150 with the associated predetermined content descriptors 40 (or 42), defined as discussed above.

For example, upon receiving a given one of the plurality of content 24 (FIG. 6), content/channel management logic 136 may automatically retrieve content descriptor menu 148 from the plurality of content and channel/service menus 138 (FIG. 6) and present it to the user. Alternately, menu 148 may be retrieved based on received user inputs. In yet another alternative, menu 148 may be utilized by a content provider 28, 30 (FIG. 1) to associate content descriptors 40, 42 with a given content, thereby defining assigned content descriptor 48, prior to receipt of content by MDS 22. In any case, a user may utilize one or more input mechanisms 112 (FIG. 6) to provide a selection indicator 152, such as a highlight, a checkmark, etc., to indicate the selection of one or more predetermined content descriptors 40, thereby defining one or more assigned content descriptors 48 for association with the given content 24.

Alternatively, or in addition, for example, a user may individually define one or more assigned content descriptors 48 by typing in a name, a description, etc. These non-standard descriptors may be, in combination with the selected predetermined content descriptors, defined as the assigned content descriptors 48 for a given one of the plurality of content 24. Further, in some aspects, content/channel management logic 136 may include algorithms, decision-making routines, fuzzy logic, heuristic relationships, neural networks, etc. which may be operable to associate non-standard content descriptors with one or more predetermined content descriptors and store this relationship as the assigned content descriptor 48.

Further, for example, content descriptor menu 148 may include selectable functions, such as "Save" virtual button 154 to save the selected content descriptors as assigned content descriptors 48 and/or an "Options" virtual button 146 to access an alternate one of the plurality of content and channel/service menus 138 (FIG. 6). For example, selection of "Options" virtual button 146 may provide access to a help menu and/or a menu to retrieve information that describes what types of features content should have to be considered for a respective descriptor, etc. As such, one or more assigned content descriptors 48 can created and/or modified, and saved for respective ones of the plurality of content 24 (FIG. 6), as may be identified by content ID 100. Further, a set of one or more content descriptors may be customized for one or more respective channels 86 and/or services 36 (FIG. 1). Thus, in some aspects, user interaction with content and channel/service menus 138 (FIG. 6) results in the generation of one or more assigned content descriptors 48, which may be associated with one or more respective channels 86 and/or services 34 (FIG. 1).

Referring back to FIG. 1, network 38 may comprise any data and/or communications network. In some aspects, for example, network 38 comprises all or some portion of a multicast network such as a Forward Link Only (FLO) network, including the above mentioned MediaFLO™ System available from Qualcomm, Inc. of San Diego, Calif. In other aspects, network 38 may include one or a combination of other networks, such as: a digital video broadcasting (DVB) network, such as DVB-S for satellite, DVB-C for cable, DVB-T for terrestrial television, DVB-H for terrestrial television for handhelds; a terrestrial telephone network; a satellite telephone network; an infrared network such as an Infrared Data Association (IrDA)-based network; a short-range wireless network; a Bluetooth® technology network; a ZigBee® protocol network; an ultra wide band (UWB) protocol network; a home radio frequency (HomeRF) network; a shared wireless access protocol (SWAP) network; a wideband network, such as a wireless Ethernet compatibility alliance (WECA) network, a wireless fidelity alliance (Wi-Fi Alliance) network, and a 802.11 network; a public switched telephone network; a public heterogeneous communications network, such as the Internet; a private communications network; and land mobile radio network.

Further, examples of telephone networks that may be included in some aspects of network 38 include one, or any combination, of analog and digital networks/technologies, such as: code division multiple access (CDMA), wideband code division multiple access (WCDMA), universal mobile telecommunications system (UMTS), advanced mobile phone service (AMPS), time division multiple access (TDMA), frequency division multiple access (FDMA), orthogonal frequency division multiple access (OFDMA), global system for mobile communications (GSM), single carrier (1X) radio transmission technology (RTT), evolution data only (EV-DO) technology, general packet radio service (GPRS), enhanced data GSM environment (EDGE), high speed downlink data packet access (HSPDA), analog and digital satellite systems, and any other technologies/protocols that may be used in at least one of a wireless communications network: and a data communications network.

Figure 9:
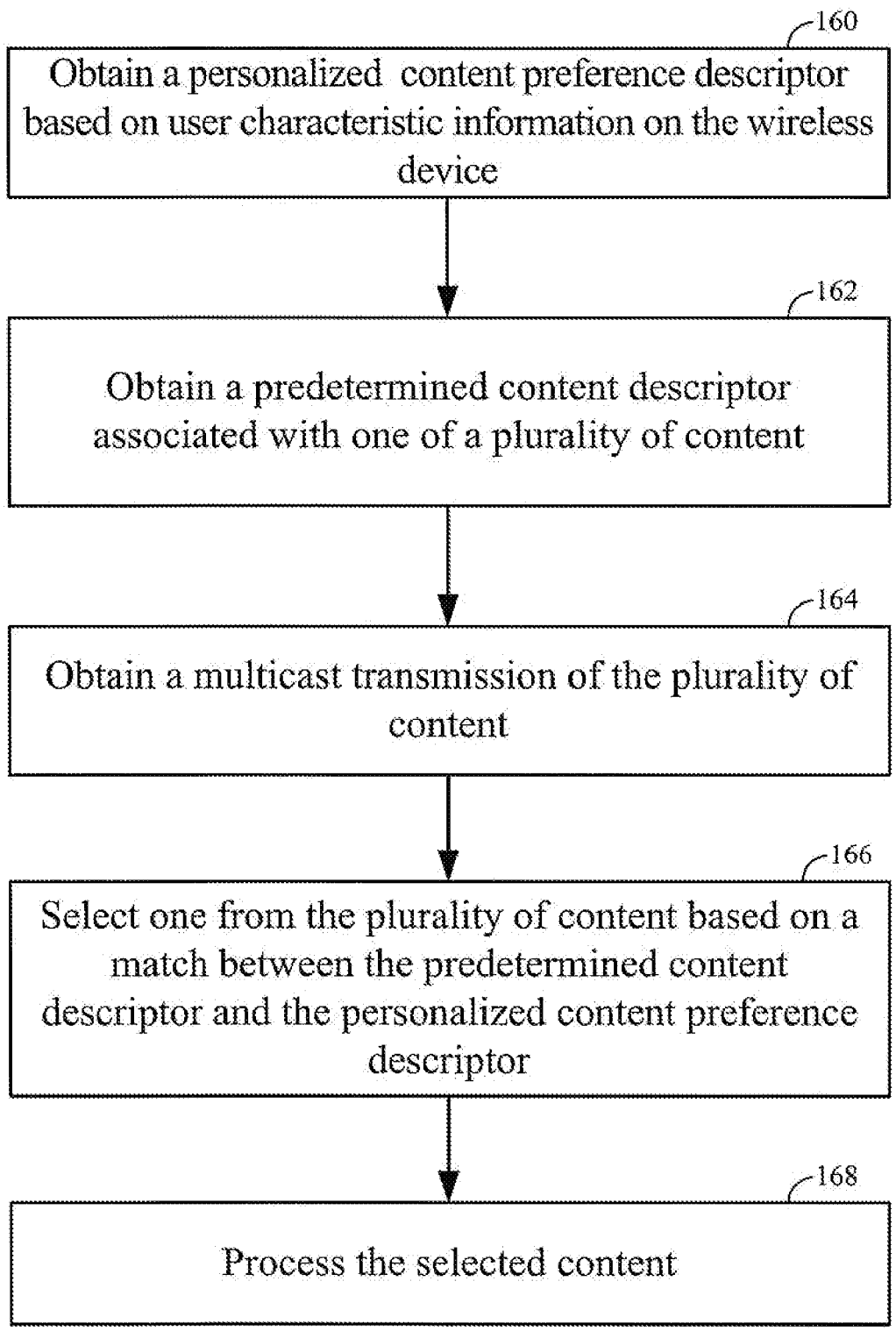
FIG. 9 is a flowchart of one aspect of a method of receiving selected content on a wireless device.

In operation, referring to FIG. 9, some aspects of receiving content comprise obtaining, on the wireless device, a personalized content preference descriptor based on user characteristic information on the wireless device (Block 160). For example, in some aspects, wireless device 25 may receive, determine and/or generate one or more user personalized content preference descriptors 52, 55, either based on user input information and/or derived from user/device behavior; both of which may be included in user characteristic information 51 stored on the respective device. In some aspects, the personalized content preference descriptor 52, 55 may correspond to a predetermined content descriptor 40, 42, such as may be defined by a content supplier.

The method further includes obtaining, on the wireless device, a predetermined content descriptor associated with or corresponding to one of a plurality of content (Block 162). For example, in some aspects, wireless device 25 may receive one or more assigned content descriptors 48 associated with one or more of the plurality of content 24 received in a multicast flow 34 from MDS 22. Furthermore, in some aspects, the predetermined content descriptors 40, 42, may vary from one service to another service, and/or from one content supplier to another content supplier.

Further, the method includes obtaining, on the wireless device, a multicast transmission of the plurality of content (Block 164). For example, in some aspects, wireless device 25 may receive one or more of the plurality of content 24 received in multicast flow 34 from MDS 22. Further, for example, multicast flow 34 may be associated with a respective one of a plurality of content suppliers.

Additionally, the method includes selecting, at the wireless device, one from the plurality of content based on a match between the predetermined content descriptor and the personalized content preference descriptor (Block 166). For example, in some aspects content selection engine 56 on wireless device 25 may identify a correspondence between one or more user personalized content preference descriptors 52 and a received one or more assigned content descriptors 48 associated with one or more of the plurality of content 24 received in the multicast flow 34 from MDS 22. Upon identifying this correspondence, content selection engine 56 extracts the respective one or more of the plurality of content 24 from flow 34, thereby defining selected content 57. Further, for example, content selection engine 56 may utilize a predetermined match threshold 99 to determine if a match exists.

Further, the method includes processing, at the wireless device, the selected content (Block 168). For example, in some aspects, media module 50 on wireless devices 25 may execute selected content 57 and present it to the device-user on user interface 62. In other aspects, the processing may include saving selected content 57 to content storage 60.

Figure 10:
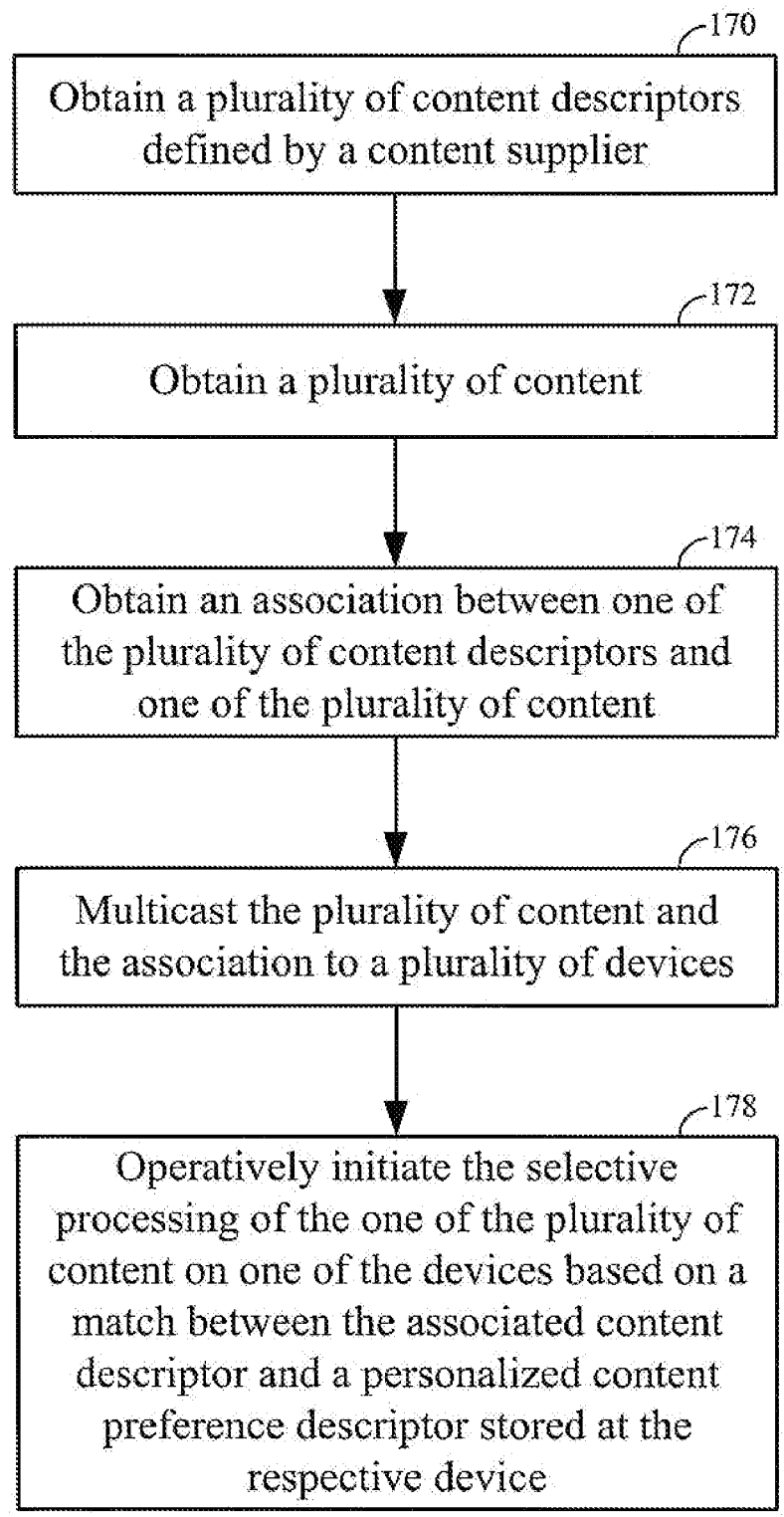
FIG. 10 is a flowchart of one aspect of a method of distributing content to a wireless device.

Referring to FIG. 10, in other aspects, a method of distributing content comprises obtaining, at a distribution system, a plurality of content descriptors defined by a content supplier (Block 170). For example, in some aspects, media distribution system 22 receives one or more predetermined content descriptors 40 and/or 42 associated with one or more service providers, such as via service ID 44 and/or 46.

The method further includes obtaining, at the distribution system, a plurality of content (Block 172). For example, in some aspects, media distribution system 22 receives one or more of the plurality of content 24 from one or more content providers 28 and/or 30.

Further, the method includes obtaining, at the distribution system, an association between at least one of the plurality of content descriptors and at least one of the plurality of content (Block 174). For example, in some aspects, content/channel manager module 134 receives inputs that define one or more assigned content descriptors 48 for one or more of the plurality of content 24. In some aspects, one or more assigned content descriptor 48 may be selected from predetermined content descriptors 40 and/or 42 associated with one or more service providers.

Additionally, the method includes multicasting the plurality of content and the association to a plurality of devices (Block 176). For example, in some aspects, MDS 22 may generate multicast transmission comprising flow 34 of one or more of the plurality of content 24 and the associated one or more assigned content descriptors 48 to one or more wireless devices 25-27.

Further, the method includes operatively initiating the selective processing of the one of the plurality of content on one of the devices based on a match between the associated content descriptor and a personalized content preference descriptor stored at the respective device (Block 178). For example, in some aspects, one or more assigned content descriptors 48 transmitted by MDS 22 in association with a respective one or more of the plurality of content 24 are utilized by content selection engine 56 on wireless device 25 to identify a match with one or more personalized content preference descriptors 52, and to then process/execute/store selected content 57 from the plurality of content 24 based on the match.

Therefore, in various aspects, the apparatus and methods of the described communication network 20 provide for the distribution of a plurality of content tagged with descriptors and a plurality of predetermined descriptors potentially associated with the content. Further, in various aspects, the apparatus and methods of the described communication network 20 provide for the retention and presentation of content selected by the wireless device from a multicast of the plurality of content based on a match between user characteristic-based descriptors, identified from the plurality of predetermined descriptors and respective tagged content. Thus, a user of a wireless device is provided with content, extracted by the wireless device from a diverse group of content, most likely to be of interest to, applicable to, and/or relevant to the user.

The various illustrative logics, logical blocks, modules, and circuits described in connection with the embodiments disclosed herein may be implemented or performed with a general purpose processor, a digital signal processor (DSP) an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternatives, the processor may be any conventional processor controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Further, the steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium is coupled to the processor, such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

While the foregoing disclosure includes illustrative aspects, it should be noted that various changes and modifications could be made herein without departing from the scope of these described aspects as defined by the appended claims. For example, although described with regard to a multicast mechanism, one or more of the described aspects may be applied to other types of broadcast systems. Further for example, although elements of the described aspects may be described as having certain associations or relationships relative to one another, it should be understood that the described element and/or its functionality may be distributed in any manner. Furthermore, although elements of the described aspects may be described or claimed in the singular, the plural is contemplated unless limitation to the singular is explicitly stated. Additionally, all or a portion of any aspect may be utilized with all or a portion of any other aspect, unless stated otherwise. Further, although specific terms are employed herein, they are used in a generic and descriptive sense only and not for purposes of strict limitation unless otherwise specified. Therefore, it is to be understood that the invention is not to be limited to the specific aspects disclosed and that modifications and other aspects are intended to be included within the scope of the appended claims.

What is claimed is:

1. A method of receiving content, comprising:
    obtaining, on a wireless device, at least one global personalized content preference descriptor and at least one content-specific personalized content preference descriptor, wherein:
        the at least one global personalized content preference description and the at least one content-specific personalized content preference descriptor are generated based on at least one of psychographic information and personality traits of other wireless device users, wherein a global personalized content preference descriptor indicates a preference of a wireless device user applicable across all content; and
        the other wireless device users are selected from the group consisting of friends identified by the wireless device user, family identified by the wireless device user, and co-workers identified by the wireless device user;
    obtaining, on the wireless device, a predetermined content descriptor for each of a plurality of content;
    receiving, on the wireless device, a multicast transmission of the plurality of content;
    identifying, on the wireless device, for each content in the plurality of content, at least one content-specific personalized content preference descriptor associated with the content;
    automatically selecting, on the wireless device, at least one content from the multicast transmission of the plurality of content based on a match between at least a portion of a predetermined content descriptor associated with the at least one content from the multicast transmission and both of the at least one global personalized content preference descriptor and at least one content-specific personalized content preference descriptor associated with the at least one content from the multicast transmission; and
    processing, on the wireless device, the selected content,
    wherein a content-specific personalized content preference descriptor indicates a preference of the wireless device user applicable to only one particular content based on a type of the one particular content.

2. The method of claim 1, wherein obtaining the at least one global personalized content preference descriptor and at least one content-specific personalized content preference descriptor comprises selecting the at least one global personalized content preference descriptor and the at least one content-specific personalized content preference descriptor from a plurality of predetermined content descriptors defined by a content supplier.

3. The method of claim 1, wherein obtaining the at least one global personalized content preference descriptor and at least one content-specific personalized content preference descriptor comprises selecting the at least one global personalized content preference descriptor and the at least one content-specific personalized content preference descriptor from a plurality of predetermined content descriptors corresponding to a respective one of a plurality of services associated with a content supplier, wherein at least two of the plurality of services are associated with a different plurality of predetermined content descriptors.

4. The method of claim 1, wherein obtaining the at least one global personalized content preference descriptor and at least one content-specific personalized content preference descriptor comprises generating the at least one global personalized content preference descriptor and the at least one content-specific personalized content preference descriptor based on at least one of information associated with a psychographic of predetermined users and information associated with predetermined users within a predetermined geographic area.

5. The method of claim 4, wherein obtaining the at least one global personalized content preference descriptor and at least one content-specific personalized content preference descriptor comprises obtaining the at least one global personalized content preference descriptor and at least one content-specific personalized content preference descriptor by executing at least a predetermined one of an algorithm, a decision-making routine, fuzzy logic, a heuristic method and a neural network.

6. The method of claim 1, wherein obtaining the at least one global personalized content preference descriptor and at least one content-specific personalized content preference descriptor comprises generating the at least one global personalized content preference descriptor and the at least one content-specific personalized content preference descriptor based on at least one of local time, a wireless network carrier associated with the wireless device and a device characteristic.

7. The method of claim 6, wherein generating the at least one global personalized content preference descriptor and at least one content-specific personalized content preference descriptor comprises obtaining the at least one global personalized content preference descriptor and at least one content-specific personalized content preference descriptor by executing at least one of a predetermined algorithm, a predetermined decision-making routine, predetermined fuzzy logic, a predetermined heuristic method and a predetermined neural network.

8. The method of claim 1, wherein processing the selected content comprises storing the selected content at the wireless device.

9. The method of claim 1, wherein selecting at least one content from the multicast transmission of the plurality of content further comprises determining if at least the portion of the predetermined content descriptor satisfies a predetermined matching threshold.

10. The method of claim 1, wherein processing the selected content comprises presenting the selected content at the wireless device.

11. A wireless device comprising:
a memory; and
a processor coupled to the memory, the processor configured with processor-executable instructions to perform the method of claim 1, 2, 3, 4, 5, 6, 8, 9 or 10.

12. A non-transitory processor-readable medium configured with processor-executable instructions to cause a processor of a wireless device to perform the method of claim 1, 2, 3, 4, 5, 6, 8, 9 or 10.

13. A method of receiving content, comprising:
obtaining, on a wireless device, at least one global personalized content preference descriptor and at least one content-specific personalized content preference descriptor;
obtaining, on the wireless device, a predetermined content descriptor for each of a plurality of content;
receiving, on the wireless device, a multicast transmission of the plurality of content;
identifying, on the wireless device, for each content in the plurality of content, at least one content-specific personalized content preference descriptor associated with the content;
automatically selecting, on the wireless device, at least one content from the multicast transmission of the plurality of content based on a match between at least a portion of a predetermined content descriptor associated with the at least one content from the multicast transmission and both of the at least one global personalized content preference descriptor and at least one content-specific personalized content preference descriptor associated with the at least one content from the multicast transmission; and
processing, on the wireless device, the selected content,
wherein a global personalized content preference descriptor indicates a preference of a wireless device user applicable across all content; and
wherein a content-specific personalized content preference descriptor indicates a preference of the wireless device user applicable to only one particular content based on a type of the one particular content.

* * * * *